United States Patent [19]

Franco et al.

[11] Patent Number: 5,270,182

[45] Date of Patent: Dec. 14, 1993

[54] ANTIBIOTIC COMPOUNDS AND THEIR PRODUCTION

[75] Inventors: Christopher M. M. Franco, Bombay; Dilip J. Upadhyay, Maharashtra; Louis E. L. Coutinho; Bimal N. Ganguli, both of Bombay, all of India; Jürgen Blumbach, Niedernhausen, Fed. Rep. of Germany; Hans-Wolfram Fehlhaber, Idstein, Fed. Rep. of Germany; Herbert Kogler, Kelkheim, Fed. Rep. of Germany

[73] Assignee: Hoechst Aktiengesellschaft, Frankfurt am Main, Fed. Rep. of Germany

[21] Appl. No.: 879,398

[22] Filed: May 7, 1992

[30] Foreign Application Priority Data

May 10, 1991 [EP] European Pat. Off. ........ 91107618.0

[51] Int. Cl.$^5$ ..................... C12P 19/60; C07H 15/26; C07D 311/78; C12R 1/465
[52] U.S. Cl. ..................... 435/75; 536/16.8; 536/16.9; 536/18.1; 536/18.2; 514/27; 514/453; 435/119; 435/886; 549/275; 549/415; 549/416
[58] Field of Search ............ 536/16.8, 16.9, 18.1, 536/18.2; 435/119, 75, 886; 514/453, 27; 549/275, 415, 416

[56] References Cited

U.S. PATENT DOCUMENTS

| | | | |
|---|---|---|---|
| 4,230,692 | 10/1980 | Sehgal et al. | 536/16.8 |
| 4,518,589 | 5/1985 | Konishi et al. | 514/27 |
| 4,598,145 | 7/1986 | Matson et al. | 536/1.1 |
| 5,064,945 | 11/1991 | Yamada et al. | 536/17.5 |
| 5,079,232 | 1/1992 | Ohsawa et al. | 536/16.8 |

FOREIGN PATENT DOCUMENTS 62-207284 9/1987 Japan .

OTHER PUBLICATIONS

M. Dobler et al., Helvetica Chimica Acta, vol. 60. Nr. 19 (1977), S. 178 ff.

S. Omura et al., J. Am. Chem. Soc., vol. 108, (1986), S. 6088 ff.
K. Kobayashi et al., J. of Antibiotics, vol. XLI, No. 6, (1988) S.741 ff.
T. M. Lee et al., J. Chem. Soc., Chem. Commun., (1989), S. 1771 ff.
W. M. Maiese et al., J. of Antibiotics, vol. XLII, No. 6, (1989) S. 846 ff.
G. T. Carter et al., J. of Antibiotics, vol. XLIII, No. 5, (1990), S. 504 ff.
Berger et al.; Chemical Abstracts 78:109258b (1973).

*Primary Examiner*—Nancy S. Husarik
*Attorney, Agent, or Firm*—Finnegan, Henderson, Farabow, Garrett & Dunner

[57] ABSTRACT

The novel compounds of formulas I and II

M 90 1809

M 90 1809H (Abstract continued on next page.)

-continued
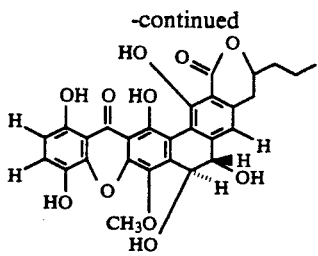
have an antibiotic activity.
II
5 Claims, 4 Drawing Sheets

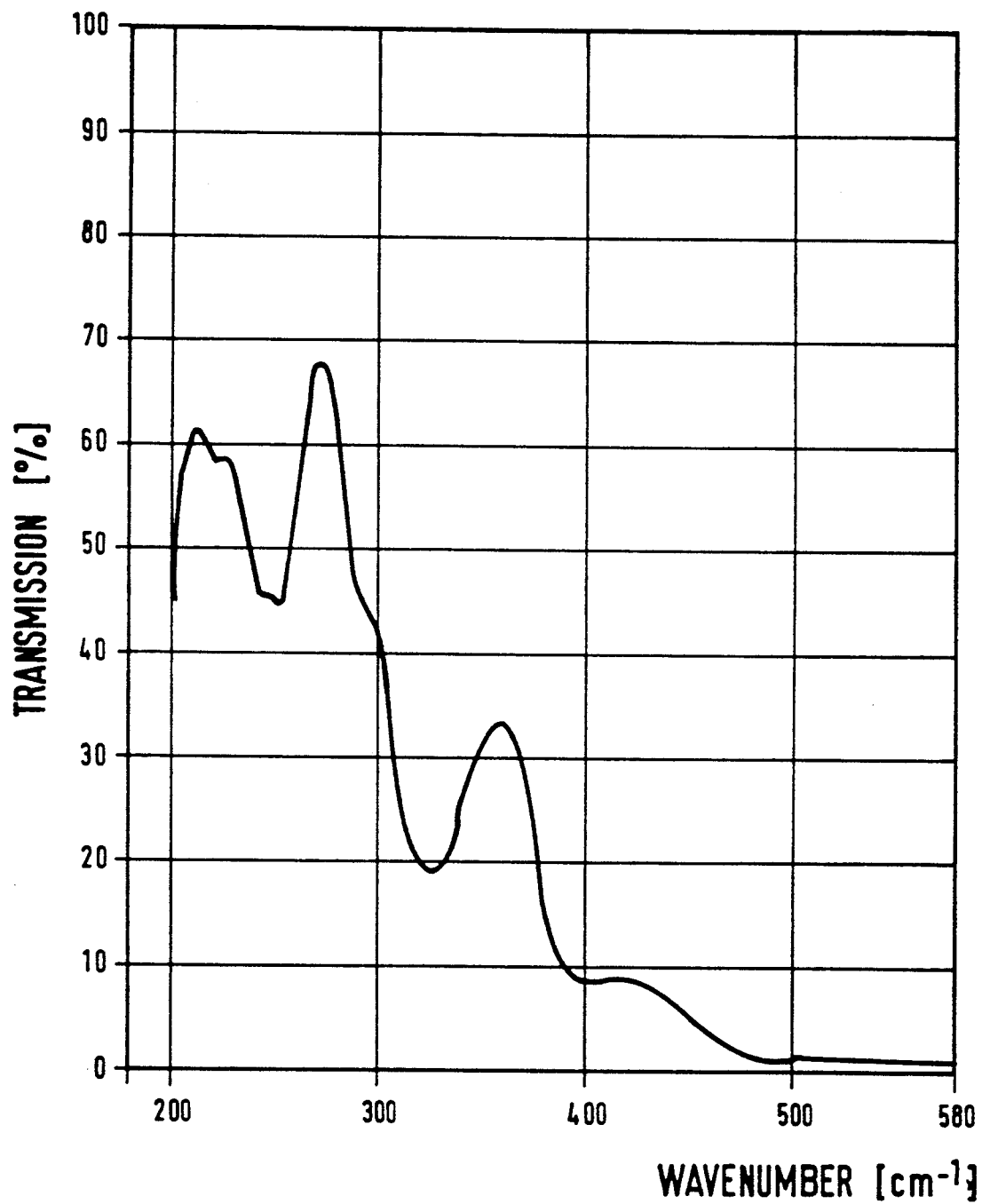
Fig. 1  UV SPECTRUM OF M90 1809

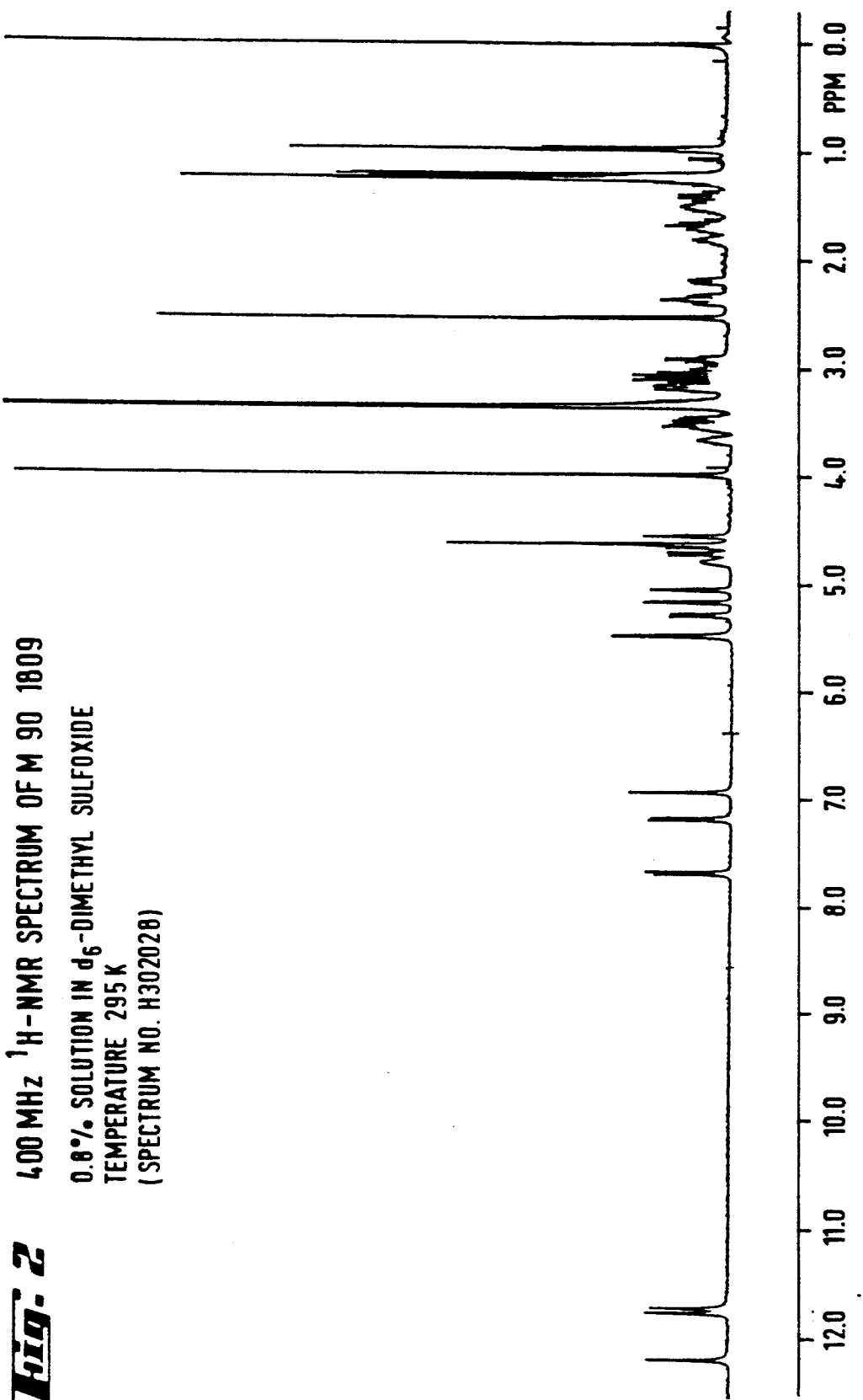

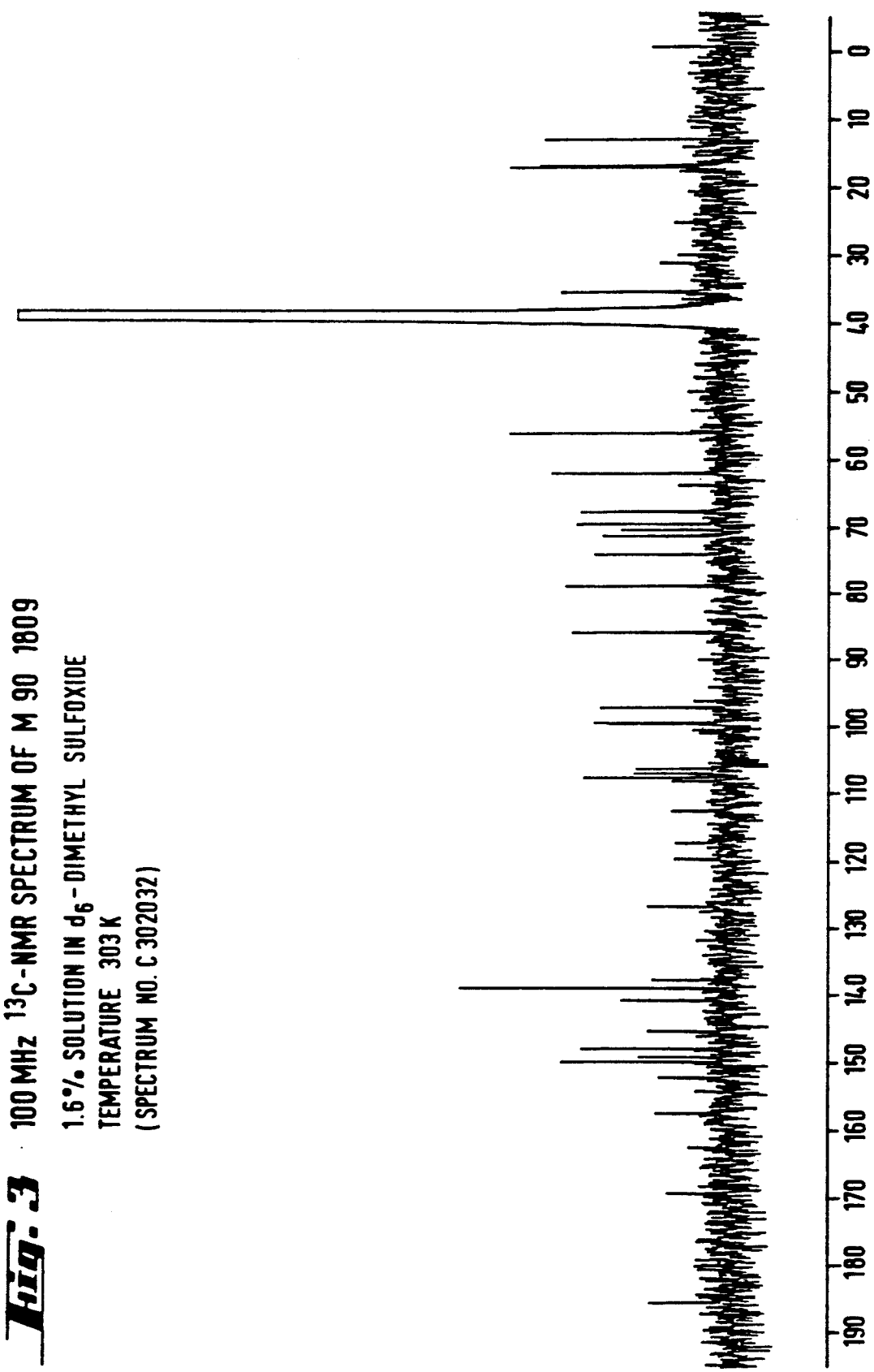

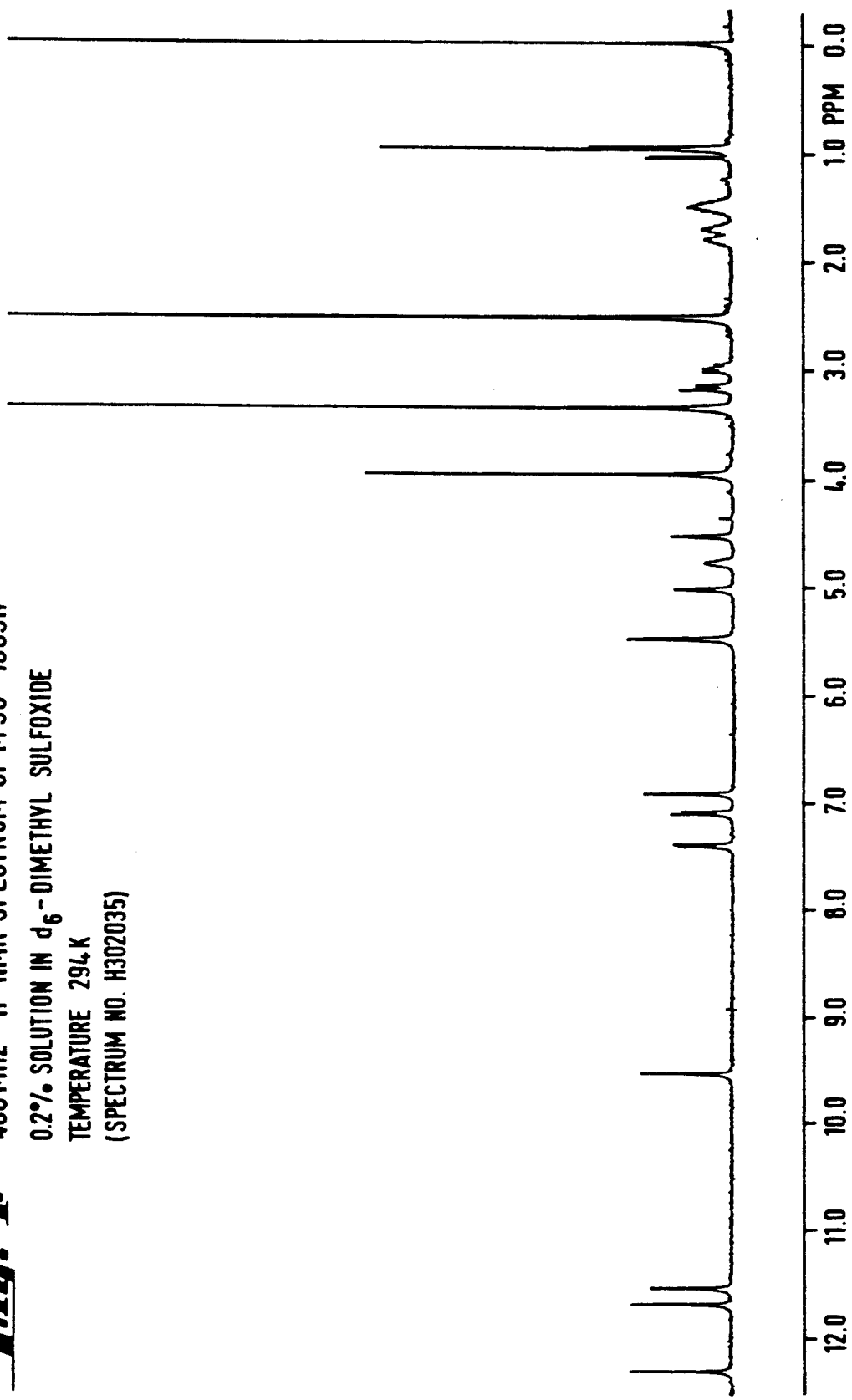

ANTIBIOTIC COMPOUNDS AND THEIR PRODUCTION

DESCRIPTION

The instant invention relates to the new compounds of formula I and II

M 90 1809

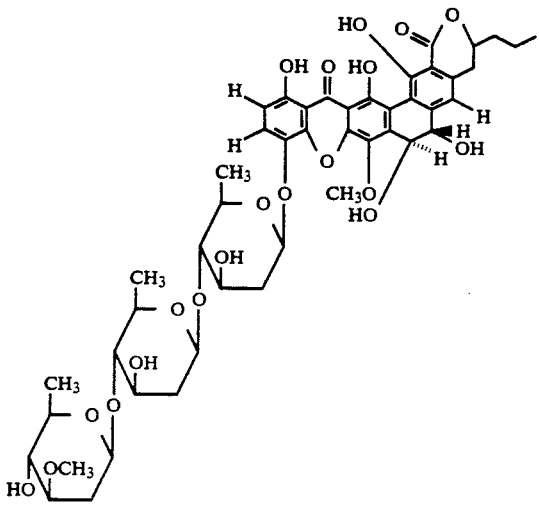

M 90 1809H

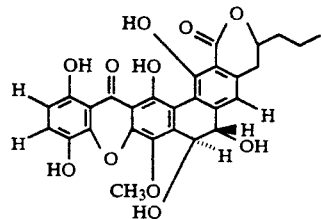

as well as to a process for their production with the help of Streptomyces species (Str. sp.) culture number HIL Y-90,31665 (Str. sp. Y-90,31665). Said microorganism has been deposited under the conditions of the Treaty of Budapest on Feb. 25, 1991 (DSM 6389).

Str. sp. Y-90,31665 was isolated from soil collected at the Bharatpur Game Reserve, Rajasthan, India. Variants and mutants of culture number HIL Y-90,31665 can be obtained in a known manner using a mutagen, such as N-methyl-N'-nitro-N-nitrosoguanidine or ultraviolet light. The microorganism Str. sp. Y-90,31665 belongs to the order Actinomycetales, family Streptomycetaceae and genus Streptomyces.

Str. sp. Y-90,31665 is considered to be a new strain since it differs from the known strains in some of its morphological, cultural and physiological characteristics. It is considered to be a new strain also because it produces a new compound herein called M901809 as will be clear from the description hereinafter.

Str. sp. Y-90,31665 can be isolated from soil using a nutrient medium at a pH of 6.5 to 8.5 in known manner.

The nutrient medium used for isolation of the microorganism from soil preferably consists of the following carbon and nitrogen sources, inorganic nutrient salts and solidifying agents. Sources of carbon may be glucose, starch, dextrin, glycerol, sucrose or molasses. Sources of nitrogen may be peptone, yeast extract, beef extract, malt extract, casein or amino acids such as arginine or asparagine. The solidifying agent may, for example, be agar. The inorganic nutrient salts may be salts of sodium, potassium, magnesium, calcium, iron, zinc, manganese, copper, phosphorous or sulphur.

The microorganism of this invention elongates colourless aerial mycelia from branched substrate mycelia. Spores are formed in straight chains on top of aerial mycelia representative of Section Spirales. Neither whirl nor ascospores are observed. Mature spore chains contain more than 30 spores per chain. Based on the cultural and morphological characteristics of the microorganism on various agar media, as well as cell wall analysis which shows the presence of LL-diaminopimelic acid, the producing organism was identified as a Streptomyces sp.

It may be well understood to those skilled in the art that this invention is not limited to the particular organism which has been specified above but includes all those spontaneous and artificial mutants and variants derived from the said microorganism which are capable of producing the new compound M901809.

The chemical structure of the compound M901809 has been elucidated from its spectroscopic data and by using two-dimersional NMR spectroscopic techniques. M901809 consists of a trisaccharide unit linked to a polycyclic xanthone containing aglycone. Under acidic conditions, M901809 can be hydrolysed to yield the aglycone M901809H which also is a novel antibiotic. Both M901809 and M901809H represent a new type of natural product.

There are several antibiotics known which exhibit the same carbon frame-work but a lactame function instead of the lactone function in ring F and, in addition, quite a different substitution pattern:

Lysolipion I: M. Dobler and W. Keller-Schierlein; Helv. Chim. Acta 60 (1977), 178.

Cervinomycin: S. Omura, A. Nakagawa, K. Kushida and G. Lukacs; J. Amer. Chem. Soc. 108 (1986), 6088.

Actinoplanones A-G: K. Kobayashi, C. Nishino, J. Ohja, S. Sato, T. Mikawa, Y. Shiobara and M. Kodama; J. Antibiotics XLI (1988), 741.

Simaomicins: T. M. Lee, G. t. Carter and D. B. Borders; J. Chem. Soc., Chem. Commun. (1989), 1771.

LL-E19085: W. M. Maiese, M. P. Lechevalier, H. A. Lechevalier, J. Korshala, J. Goddmann, M. J. Wildey, N. Kuck and M. Greenstein; J. Antibiotics XLII (1989), 846.

Citreaminicins: G. T. Carter, J. A. Nietsche, D. R. Williams and D. B. Borders; J. Antibiotics XLIII (1990), 504.

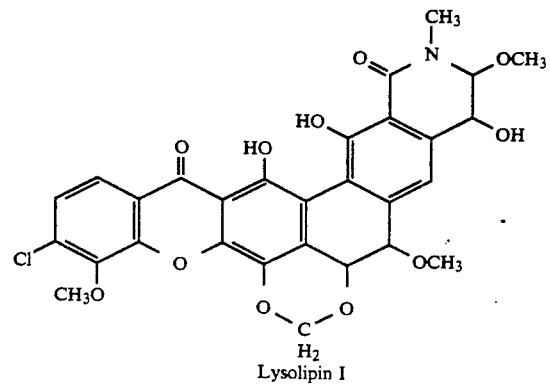

Lysolipin I

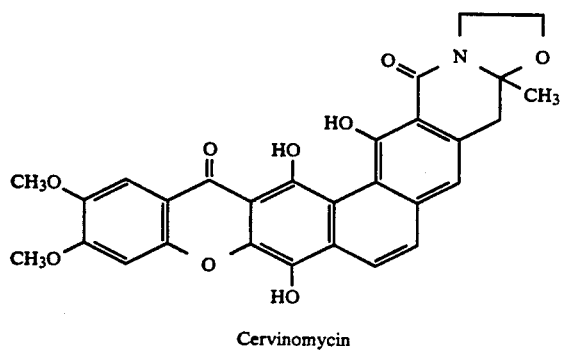

Cervinomycin

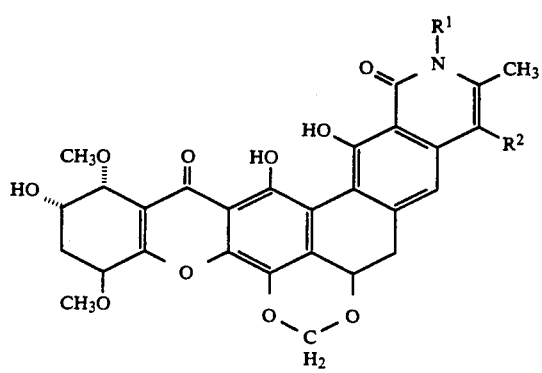

R₁=H, NH₂, N=C(CH₃)₂, N=C(CH₃)COCH₃
R₂=H, Cl

Actinoplanones A–G

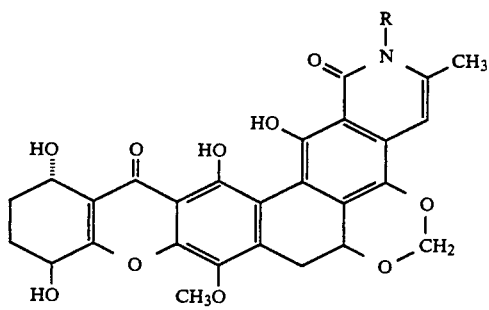

R=H, CH₃

Simaomicins α and β

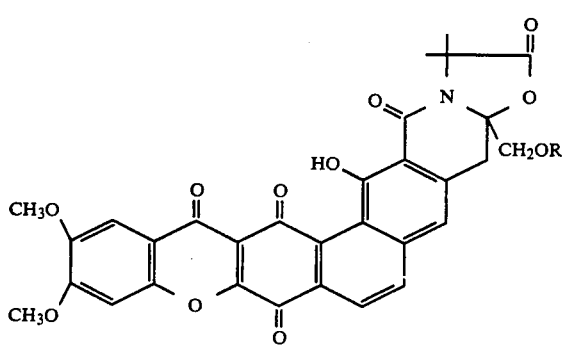

R=COCH₂CH(CH₃)₂
LL-E19085α

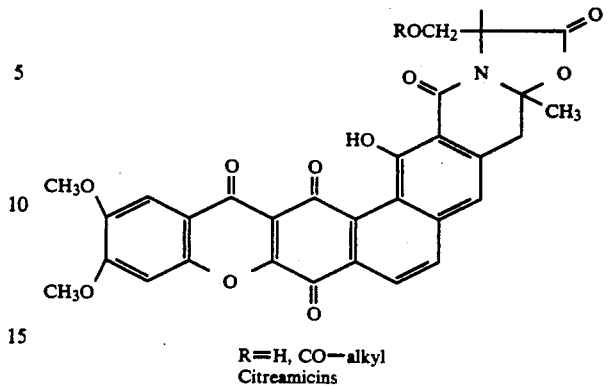

R=H, CO—alkyl

Citreamicins

According to the present invention there is also provided a process for the production of M901809 which contains the novel aglycone M901809H, said process comprising cultivating Str. sp. Y-90,31665 by fermentation at a pH between 6.0 and 8.0 and a temperature between 20°–40° C. under aerobic conditions in a nutrient medium containing sources of carbon and nitrogen, nutrient inorganic salts, and trace elements, and isolating the compound from the culture broth in a known manner such as herein described.

The carbon sources used in the nutrient medium for the production of the novel compounds may be for instance starch, dextrin, glycerol, sucrose, molasses or oil. Sources of nitrogen used in the nutrient medium for production of the novel antibiotics may be for instance soyabean meal, yeast extract, beef extract, malt extract, cornsteep liquor, peptone, gelatin or casein. Nutrient inorganic salts/mineral salts used in the nutrient medium for production of the novel antibiotics may be e.g. sodium chloride, magnesium sulphate, ammonium sulphate or calcium carbonate. As trace elements, for example iron, manganese, copper, zinc or cobalt may be used.

Preferably Str. sp. Y-90,31665 is cultivated at 27° C. and pH 7.2. The fermentation is preferably stopped after 66–72 hours when maximum yields of the compounds are obtained. The fermentation may, preferably, be submerged fermentation. The process of fermentation and formation of the novel compound can be monitored by the antibacterial activity of the culture fluid and mycelium against Staphylococcus aureus 209 P in agar medium and by thin layer chromatography on silica gel plates with ethyl acetate as developing solvent.

If desired, an antifoaming agent such as Desmophen® (Polyols, Bayer AG, Leverkusen, Germany) may be used in the nutrient medium during fermentation of the culture.

Compound M901809 is found predominantly in the mycelium and can be extracted out using an organic solvent such as methanol, acetone, acetonitrile, chloroform or ethyl acetate. The preferred solvent is acetone. After concentration of the mycelium extract the aqueous concentrate is diluted with water and extracted with a water-immiscible solvent such as butanol, ethyl acetate or chloroform. The preferred solvent is ethyl acetate. Antibiotic M901809 is also obtained from the culture filtrate by extraction with a water-immiscible solvent after the pH has been adjusted to 6.8–7.2. The solvents could be ethyl acetate or chloroform; preferably, it is ethyl acetate and the preferred pH is 7.0. The solvent extracts of the mycelium and the culture filtrate are concentrated to remove the solvent and then chromatographed further. Compound M901809 can also be obtained from the culture broth by direct adsorption on suitable adsorbents such as Amberlite® XAD-4 or 7 (Rohm and Haas Co., U.S.A.), or Diaion® HP-20 (Mitsubishi Chemical Industries, Japan); the preferred adsorbent being Diaion® HP-20. The compound according to the invention is eluted from the adsorbent using appropriate mobile phases, such as methanol or acetone, either singly, in combination with each other, or with water, and the eluates are then evaporated to dryness. The preferred eluant is methanol. The active eluates thus obtained are pooled and concentrated.

The aforementioned concentrated eluates or extracts containing compound M901809, can be further purified in a number of ways. For example, re-adsorption and elution processes with activated carbon, Amberlite® XAD-4 and 7 or Diaion® HP-20; gel filtration with Sephadex® LH-20 gel (Pharmacia Fine Chemicals AB, Sweden) and its equivalents; adsorption chromatography on alumina and silica gel, can be conveniently combined for further purification. In addition, thin-layer chromatography, medium-pressure and high-pressure liquid chromatography using suitable adsorbents such as silica gel and modified silica gel-$C_{18}$ with suitable solvent systems may be used. Furthermore, counter current chromatography with a particular biphasic solvent system may work well for the said purpose. Preferably, silica gel chromatography with dichloromethane and ethyl acetate as the eluting solvents is used. Another purification process used either alone, or in combination with the abovementioned purification procedures, is based on the differential solubility of compound M901809 in organic solvents. The aforementioned concentrated extracts or eluates containing compound M901809 may be precipitated with hexane or petroleum ether, repeatedly, in a known manner.

Compound M901809 may also be washed with methanol:water (99:1) and methanol:ethyl acetate (1:1) to remove impurities. Finally, compound M-901809 may be crystallized in a suitable solvent, or mixture of solvents.

Hydrolysis of compound M901809 using acidic conditions yields the acid hydrolysis product M901809H. The acids used may be acetic acid, sulfuric acid, hydrochloric acid, nitric acid or phosphoric acid. The hydrolysis may be carried out directly in the acid of various strengths, or in combination with organic solvents such as methanol, acetone or acetonitrile, with or without heating. The preferred method involves refluxing of M901809 with methanol:HCl (1:1).

The aglycone M901809H may be recovered from the reaction mixture by distillation under reduced pressure to remove the solvent. The residue is washed with water and extracted with a water-immiscible solvent such as dichloromethane. Chromatography of the concentrated dichloromethane extract over silica gel using a dichloromethane to ethyl acetate gradient gives the pure M901809H.

TABLE I

Phisico-chemical properties of compound M901809 and its acid hydrolysis product M901809H

| | M901809 | M901809H |
|---|---|---|
| 1. Appearance | Yellow powder | Yellow powder |
| 2. Solubility | Insoluble in $H_2O$, hexane and | Insoluble in $H_2O$, hexane and petroleum |

TABLE I-continued

Phisico-chemical properties of compound M901809 and its acid hydrolysis product M901809H

| | | |
|---|---|---|
| | petroleum ether (40–60° C.) | ether (40–60° C.) |
| | Poor to moderate in MeOH, $CH_3CN$ and ethyl acetate | Very soluble in MeOH, $CH_3CN$, DMSO, $CH_2Cl_2$ ethyl acetate and $CHCl_3$ |
| | Very soluble in DMSO, $CH_2Cl_2$ and $CHCl_3$ | |
| 3. Melting pt. | >250° C. | 136–139° C. |

4. Thin layer chromatography (TLC) systems:
TLC plate: Precoated silica gel plate: Article No. 5554 from E. Merck, Darmstadt.

| Rf in | M901809 | M901809H |
|---|---|---|
| Ethyl acetate | 0.15 | 0.44 |
| $CH_2Cl_2$:MeOH (9:1) | 0.62 | 0.58 |

5. High pressure liquid chromatography (HPLC):
Column packing: ODS-Hypersil® – 10μ, 4 × (30 + 100) mm
Flow Rate: 1.0 ml/min
Detection: 220 nm or 270 nm
Solvent: $CH_3CN$:$H_2O$ (3:7)
$R_T$ of M901809: 4.2 min.

6. UV $_{max}$(methanol): 228, 272, 360 & 420 nm; for M901809 and M901809H No shift in 0.1N NaOH-methanol or 0.1N HCl-methanol. The UV absorption spectrum was measured in the range 200 to 800 nm using a Uvikon 810 Spectrophotometer.

The UV spectrum of M901809 is shown in FIG. 1 of the accompanying drawings.

| | M901804 | M901804H |
|---|---|---|
| 7. $^1$H-NMR spectrum | See FIG. 2 | See Fig. 4 |
| Using a 400 MHz Bruker AM-400WB | of the accompanying drawings | |
| 8. $^{13}$C-NMR spectrum: | See FIG. 3 | |
| Using a Bruker AM-400-WB instrument. With broad band decoupling | of the accompanying drawings | |
| 10. Molecular Formula: | $C_{47}H_{56}O_{20}$ | $C_{26}H_{24}O_{11}$ |

Performed on a VG ZAB 3F instrument using High Resolution - Fast Atom Bombardment (HR-FAB) mode of ionization in the positive ion mode.

The above data was subjected to a CAS (Chemical Abstract Service) On-Line search which proved that compounds M901809 and M901809H are novel.

Compound M901809 and its acid hydrolysis product M901809H are active against gram-positive bacteria. The minimum inhibitory concentrations (MIC) of both compounds, determined by the agar-dilution method in Mueller-Hinton agar, are shown in Table II below:

TABLE II

Biological Activity of compound M901809 MIC - μg/ml

| No. | Test Organism | M901809 | M901809H |
|---|---|---|---|
| 1. | Staph. aureus 209 P | 0.1 | 1.6 |
| 2. | Staph. aureus 3066 | 0.2 | 3.2 |
| 3. | Staph. aureus 20424 a | 0.2 | 3.2 |
| 4. | Staph. aureus 20240 b | 0.2 | 3.2 |
| 5. | Staph. aureus 789 | 0.1 | 3.2 |
| 6. | Staph. aureus E 88 | 0.2 | 3.2 |
| 7. | Staph. aureus E 121 | 0.2 | 3.2 |
| 8. | Staph. aureus 011UC5 | 0.1 | 1.6 |
| 9. | Staph. aureus 690 | 0.2 | 3.2 |
| 10. | Staph. aureus 694 | 0.2 | 3.2 |
| 11. | Staph. aureus 706 | 0.2 | 3.2 |
| 12. | Staph. aureus 710 | 0.2 | 3.2 |

TABLE II-continued

Biological Activity of compound M901809
MIC - μg/ml

| No. | Test Organism | M901809 | M901809H |
|---|---|---|---|
| 13. | Staph. aureus 712 | 0.2 | 3.2 |
| 14. | Staph. aureus 722 | 0.2 | 3.2 |
| 15. | Staph. aureus 725 | 0.1 | 3.2 |
| 16. | Staph. aureus Co. 1 | 0.1 | 1.6 |
| 17. | Staph. aureus C 31153 | 0.1 | 3.2 |
| 18. | Staph. epidermidis 823 c | 0.4 | 3.2 |
| 19. | Staph. epidermidis 825 c | 0.8 | 3.2 |
| 20. | Staph. epidermidis 109 | 0.4 | 3.2 |
| 21. | Staph. epidermidis 607 | 0.4 | 3.2 |
| 22. | Staph. epidermidis 178 | 0.2 | 3.2 |
| 23. | Staph. epidermidis 291 | 0.2 | 3.2 |
| 24. | Staph. epidermidis 2 Tub | 0.2 | 3.2 |
| 25. | Staph. haemolyticus 809 | 0.4 | 3.2 |
| 26. | Staph. haemolyticus 712 | 0.2 | 1.6 |
| 27. | Ent. faecium van $R_1$ cd | 1.6 | 3.2 |
| 28. | Ent. faecalis Eder | 0.4 | 3.2 |
| 29. | Ent. faecalis 21777 | 0.4 | 3.2 |
| 30. | Ent. faecalis D 65 | 1.6 | 3.2 |
| 31. | Ent. faecalis 734 | 0.4 | 3.2 |
| 32. | Ent. faecalis 782 | 0.4 | 3.2 |
| 33. | Ent. faecalis 26777 | 0.4 | 3.2 |
| 34. | Ent. faecalis 3903 | 0.4 | 3.2 |
| 35. | Ent. faecalis UD8b | 0.8 | 3.2 | a = Erythromycin resistant
b = β-lactam resistant
c = Teicoplanin resistant
d = Vancomycin resistant Strains 5 to 26 are methicillin resistant staphylococci. In addition compound M901809 was also found active in the treatment of experimental animals infected with staphylococci and streptococci.

The invention will be further illustrated by preferred examples and by the content of the patent claims.

EXAMPLE I

Isolation of Streptomyces sp. Y-90,31665 from Soil (a) Preparation of nutrient isolation media

| Medium 1: | Starch | 10.0 g |
|---|---|---|
| | Casein | 0.3 g |
| | $KNO_3$ | 2.0 g |
| | NaCl | 2.0 g |
| | $K_2HPO_4$ | 2.0 g |
| | $MgSO_4.7H_2O$ | 0.05 g |
| | $CaCO_3$ | 0.02 g |
| | $FeSO_4.7H_2O$ | 0.01 g |
| | Agar | 15.0 g |
| | Distilled water | 1 liter |
| | pH | 7.2-7.5 |

The media were sterilised at 121° C. for 30 minutes. In all cases, the sterilized media were cooled to 45° C., poured into petri plates and allowed to solidify.

(b) Preparation of soil suspension

One gram of soil was suspended in distilled water and shaken well. The soil was allowed to settle and the supernatent fluid was used to inoculate each one of the above mentioned isolation media at a time.

(c) Inoculation of the isolation medium

One ml of the soil suspension was inoculated onto petri dishes containing 50 ml of any of the above mentioned nutrient isolation media.

(d) isolation of Streptomyces sp. Y-90,31665

The inoculated petri dish was incubated at 30° C. for 10 days and Streptomyces sp. Y-90,31665 isolated from among the growing microorganisms.

EXAMPLE II

Cultivation of Streptomyces sp. Y-90,31665 for the Fermentive Production of Compound M901809

Streptomyces sp. Y-90,31665 was maintained on yeast extract-malt extract having the following composition:

| Malt extract | 10.0 g |
|---|---|
| Yeast extract | 4.0 g |
| Glucose | 4.0 g |
| Agar | 15.0 g |
| Distilled water | 1 liter |
| pH | 7.0 |

The medium was distributed in test tubes and sterilized at 121° C. for 30 minutes. The tubes were cooled in a slanting position for preparation of agar slants. The slants were inoculated with the culture and incubated at 28° C. for 10-15 days when good growth and sporulation were observed. A suspension of the spores in distilled water from one slant was used to inoculate five 500 ml Erlenmeyer flasks each containing 100 ml of the seed culture medium.

| Composition of the seed culture medium | |
|---|---|
| Glucose | 15.0 g |
| Soyabean meal | 15.0 g |
| Cornsteep liquor | 5.0 g |
| $CaCO_3$ | 2.0 g |
| NaCl | 5.0 g |
| Distilled water | 1 liter |
| pH | 6.5 |

Three liters of the above medium was distributed in 100 ml amounts in 500 ml Erlenmeyer flasks and sterilized at 121° C. for 30 minutes. The flasks were cooled, inoculated with spore suspension or mycelial plugs and shaken at 240 r.p.m. for 72 hours at 27° (+1° C.) on a rotary shaker with 1.5 inch throw. The resultant growth was used to inoculate the 100 L fermenter containing 85 L of the production culture medium at 3% (v/v).

| Composition of the production medium | |
|---|---|
| Glucose | 20.0 g |
| Soyabeanmeal | 10.0 g |
| $CaCO_3$ | 0.2 g |
| $K_2HPO_4$ | 0.5 g |
| $CoCl_2.6H_2O$ | 1.0 mg |
| Distilled water | 1 liter |
| pH | 7.2 |

35 ml of Desmophen ® was added as antifoam agent to 85 L of the production medium taken in a 100 L fermenter. The medium was sterilized through direct and indirect steam for 20 minutes at 121° C. The fermenter was cooled and inoculated with seed culture (3% v/v). The fermentation was carried out at 27° C. (±1° C.) under stirred conditions at 100 r.p.m. with aeration at a rate of 60 liters per minute. When fermentation was discontinued at the end of 66 hours the pH of the culture broth was pH 6.7. The diameter of the zone of inhibition, when tested by the agar well method, versus *Staphylococcus aureus* 209 P and *Micrococcus luteus* was 11 and 15 mm respectively when the culture filtrate was tested, and 14 and 16 mm respectively when mycelium extract. The packed cell volume was 18%

(v/v). The culture broth was processed as in Example III.

EXAMPLE III

Isolation and Purification of Compound M901809

The culture filtrate (75 liters) from the fermentation as outlined in Example II, was extracted with 45 liters of ethyl acetate at pH 7.0 using a Westphalia ® counter current extractor. The ethyl acetate extract was concentrated to dryness to give 35 g crude extract. The mycelium (3.5 kg. wet weight) was extracted twice with 20 liters each of acetone. The acetone extract was concentrated to remove the organic solvent and then diluted to 25 liters with distilled water, followed by extraction twice with 15 liters each of ethyl acetate. This second extraction yielded 165 g of crude mycelium extract. The crude extracts were pooled, dissolved in a minimum amount of dichloromethane, and charged onto a 4.5×40 cm glass column packed with silica gel (200–300 mesh). The column was eluted with a dichloromethane to ethyl acetate gradient. At a dichloromethane:ethyl acetate ratio of 70:30 an unidentified neutral macrolide antibiotic was isolated. When the ratio was 50:50 to 40:60 the known macrolide antibiotic chalcomycin was obtained. Compound M901809 began to elute out when the ratio of the said solvents was 10:90 and eluted out completely with 100% ethyl acetate. The yellow powder obtained (4.2 g) was washed first with two 100 ml volumes of petroleum ether (40°–60° C.), then with two 50 ml volumes of methanol, and finally with 50 ml of an ethyl acetate:methanol (1:1) mixture to afford 2.0 g pure compound M901809. M901809 is identified on the basis of its physico-chemical properties and biological activity as described in Tables I and II.

EXAMPLE IV

Preparation of the Acid Hydrolysis Product M901809H

M901809 (2 g) was dissolved in MeOH (50 ml) to which was added 50 ml of conc. HCl. The reaction mixture was refluxed on a water bath for 3 hours after which the solvent mixture was distilled under reduced pressure to remove all the solvent. The residue was washed with 2×25 ml of distilled water and then extracted with 25 ml $CH_2Cl_2$. The $CH_2Cl_2$ layer was separated, concentrated under vacuum and dried. The concentrate was loaded onto a 2×30 cm glass column containing 50 g silica gel 200–300 mesh in $CH_2Cl_2$. The column was eluted with a $CH_2Cl_2$:ethyl acetate gradient with increasing amounts of ethyl acetate, M 901809H eluted out when the ratio of $CH_2Cl_2$:ethyl acetate was 50:50 to yield 600 mg of the pure compound. M901809H is identified on the basis of its physico-chemical properties and biological activity as described in Table I and II.

We claim:

1. Compounds of formula I or formula II

M 90 1809

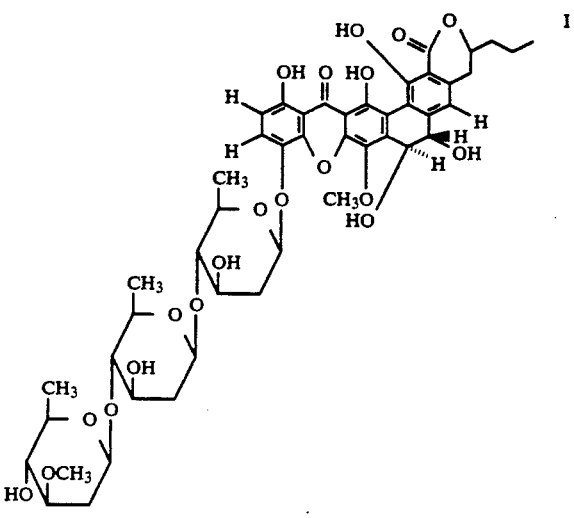

M 90 1809H

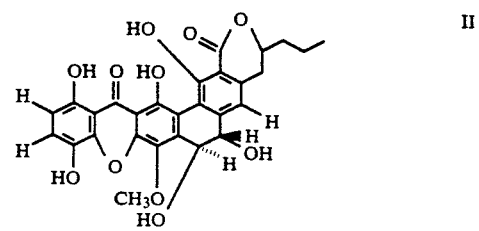

2. A process for the preparation of the compound of formula I as claimed in claim 1, which comprises cultivation of Streptomyces species Y-90,31665 under aerobic conditions in an aqueous nutrient medium which contains carbon sources, nitrogen sources, inorganic nutrient sources and trace elements and isolating the compound from the culture broth.

3. A process as claimed in claim 2, wherein the cultivation is carried out at a pH between 6 and 8 and at a temperature between 20° and 40° C.

4. A process as claimed in claim 2, wherein the cultivation is carried out at pH about 7.2 and a temperature about 27° C.

5. A process as claimed in claim 2, wherein the cultivation is stopped after 66–72 hours.

* * * * *